United States Patent
Hogan et al.

(10) Patent No.: US 8,200,306 B2
(45) Date of Patent: Jun. 12, 2012

(54) CORRELATION OF PROFILE TEMPLATES AND ACQUIRED DATA SETS

(75) Inventors: Josh N. Hogan, Los Altos, CA (US); Carol Jean Wilson, San Jose, CA (US)

(73) Assignee: Compact Imaging, Inc.

( * ) Notice: Subject to any disclaimer, the term of this patent is extended or adjusted under 35 U.S.C. 154(b) by 1365 days.

(21) Appl. No.: 11/818,309

(22) Filed: Jun. 13, 2007

(65) Prior Publication Data

US 2007/0260128 A1    Nov. 8, 2007

Related U.S. Application Data

(63) Continuation-in-part of application No. 11/254,965, filed on Oct. 19, 2005, now Pat. No. 7,248,907.

(60) Provisional application No. 60/621,366, filed on Oct. 23, 2004, provisional application No. 60/621,417, filed on Oct. 23, 2004.

(51) Int. Cl.
*A61B 5/00* (2006.01)
*A61B 6/00* (2006.01)
*G01B 9/02* (2006.01)

(52) U.S. Cl. ........ 600/316; 600/310; 600/473; 600/476; 356/450; 356/456

(58) Field of Classification Search .................. 600/310, 600/316, 322, 331, 336, 473, 475, 476; 700/57–59; 702/19; 356/456, 479, 497
See application file for complete search history.

(56) References Cited

U.S. PATENT DOCUMENTS

| | | | | |
|---|---|---|---|---|
| 5,676,143 | A  * | 10/1997 | Simonsen et al. | 600/316 |
| 6,704,589 | B1 * | 3/2004  | Oppelt et al.   | 600/407 |
| 2003/0028100 | A1 * | 2/2003 | Tearney et al. | 600/431 |
| 2003/0236458 | A1 * | 12/2003 | Hochman       | 600/431 |
| 2006/0264719 | A1 * | 11/2006 | Schurman et al. | 600/316 |

* cited by examiner

*Primary Examiner* — Eric Winakur
*Assistant Examiner* — Chu Chuan (JJ) Liu

(57) ABSTRACT

A non-invasive imaging and analysis system suitable for measuring attributes of a target, such as the blood glucose concentration of tissue, includes an optical processing system which provides a probe and reference beam. It also includes a means that applies the probe beam to the target to be analyzed, combines the probe and reference beams interferometrically and detects concurrent interferometric signals. The invention includes fitting multiple sets of concurrently acquired data to a profile template and calculating a variance between the profile template and the acquired data sets. It further includes refining the profile template to minimize the variance between at least some of the concurrently acquired data sets to generate a refined profile, correlating the refined profile with data from a data bank stored in memory and processing resulting correlation data to determine an attribute of the target.

17 Claims, 4 Drawing Sheets

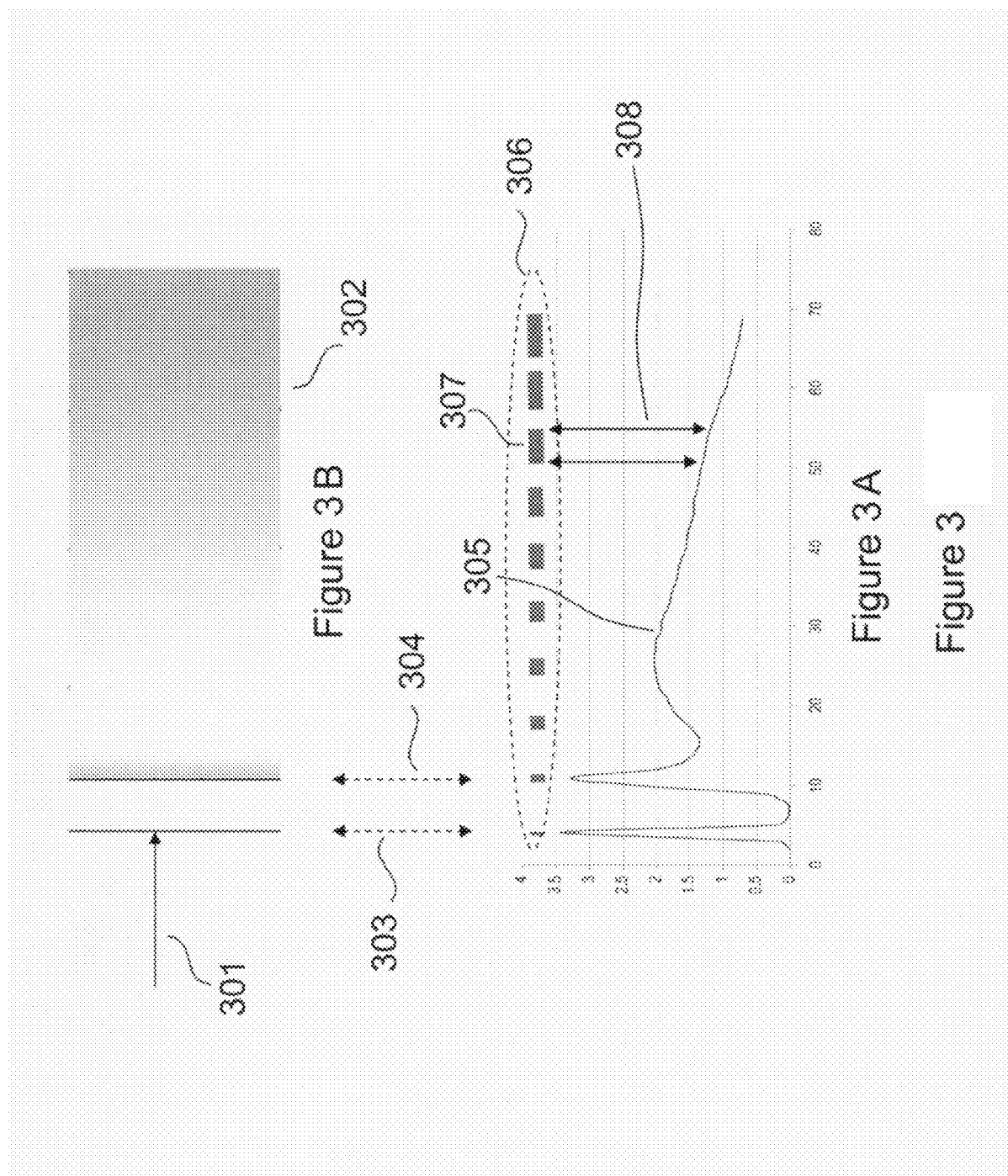

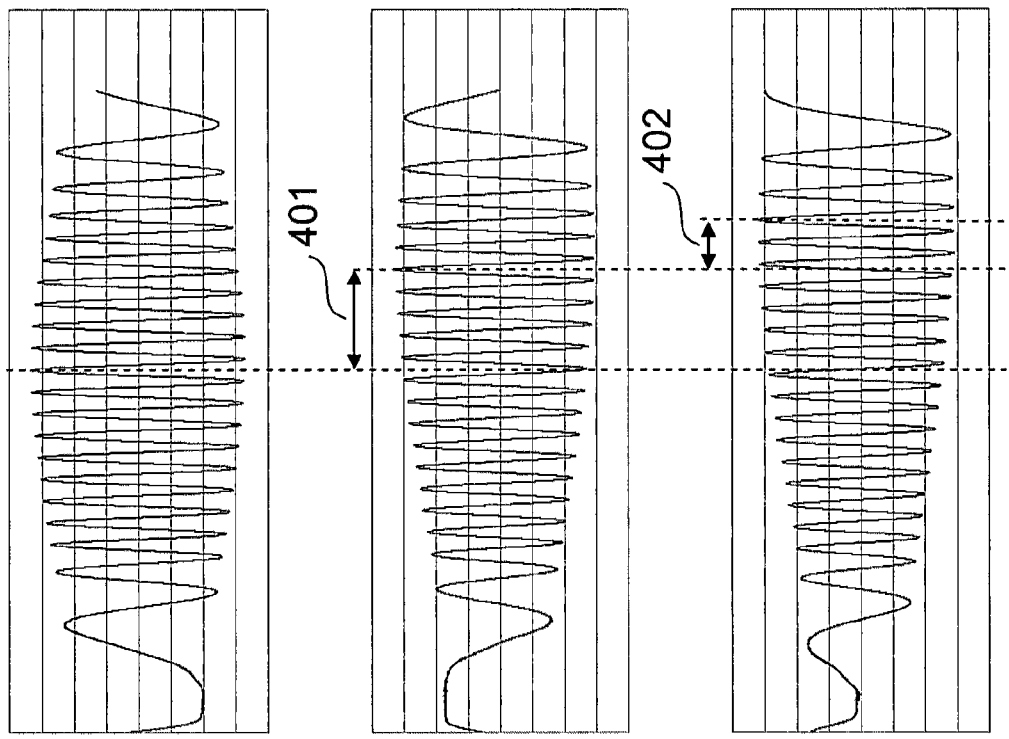

CORRELATION OF PROFILE TEMPLATES AND ACQUIRED DATA SETS

CROSS REFERENCES TO RELATED APPLICATIONS

This application 11/818,309, is a continuation-in-part of pending U.S. application Ser. No. 11/254,965, titled "Correlation of Concurrent Non-invasively Acquired Signals" filed on Oct. 19th. 2005 now U.S. Pat. No. 7,248,907, the contents of which are incorporated by reference as if fully set forth herein. U.S. application Ser. No. 11/254,965 claims priority from U.S. provisional applications No. 60/621,366 titled "Parallel three dimensional analysis system" filed on Oct. 23, 2004 and also from U.S. provisional application Ser. No. 60/621,417 titled "High speed parallel depth analysis system" filed on Oct. 23, 2004.

FIELD OF THE INVENTION

The invention relates to non-invasive analysis in general and in particular to optical non-invasive analysis of biomedical targets such as, tissue, organs and tooth material. This invention also relates to non-destructive defect analysis and verification of the authenticity of documents.

BACKGROUND OF THE INVENTION

This application relates to non-invasive analysis. It also relates to utility patent application Ser. No. 11/025,698 filed on Dec. 12th. 2004 titled "Multiple Reference Non-invasive Analysis System" and to utility patent application Ser. No. 11/048,694 filed on Jan. 31 st. 2005 titled "Frequency Resolved Imaging system the contents of both of which are incorporated by reference as if fully set forth herein.

Non-invasive analysis, which for purposes of this application includes non-destructive analysis, is a valuable technique for acquiring information about systems or targets without undesirable side effects, such as damaging the system being analyzed. Non-invasive analysis has a broad range of applications including, non-destructive analysis of artifacts for defects, verification of the authenticity of documents, such as bank notes, bio-metric analysis and bio-medical analysis of living entities.

In the case of analyzing living entities, such as human tissue, undesirable side effects of invasive analysis include the risk of infection along with pain and discomfort associated with the invasive process.

The application of which this is a continuation-in-part, U.S. application Ser. No. 11/254,965 titled "Correlation of Concurrent Non-invasively Acquired Signals" (referenced above), describes a method, apparatus and system for non-invasive analysis that is suitable for determining attributes of targets, such as concentrations of specific components or analytes within a target, including the concentration of glucose within human tissue.

The invention includes an optical source and an optical processing system which provides probe and reference radiation. It also includes a means that applies the probe beam to the target to be analyzed, re-combines the probe and reference beams interferometrically, to generate concurrent interferometric signals which are detected and correlated with previously stored electronic data to determine an attribute of the target.

Frequently, such concurrently acquired signals are modified by various unwanted interfering effects of the environment in which the signals are acquired. Interfering effects include: relative motion between the target and the non-invasive analysis system; compression of the target; variations in the intensity of radiation scattered at the surface of the target; effectively introduce noise into the acquired signals.

The effective noise introduced by these interfering effects reduce the accuracy with which the sets of concurrently acquired signals can be correlated with data from a data bank stored in memory. Therefore there is an unmet need for a method, apparatus and system for reducing the influence of the interfering effects and increasing the accuracy of correlation of the sets of concurrently acquired data and thereby determining the attribute of a target with increased accuracy.

SUMMARY OF THE INVENTION

The invention is a method, apparatus and system for non-invasive analysis. It is suitable for determining attributes of targets, such as concentrations of specific components or analytes within a target, including the concentration of glucose within human tissue. The invention includes fitting multiple sets of concurrently acquired data to a profile template and calculating a variance between the profile template and the acquired data sets. It further includes refining the profile template to minimize the variance between at least some of the concurrently acquired data sets to generate a refined profile, correlating the refined profile with data from a data bank stored in memory and processing resulting correlation data to determine an attribute of the target.

BRIEF DESCRIPTION OF THE DRAWINGS

FIG. 3 illustrates a target and a suitable profile template.

FIG. 4 illustrates time domain scans at the surface of the target.

DETAILED DESCRIPTION OF THE INVENTION

Figure 1:
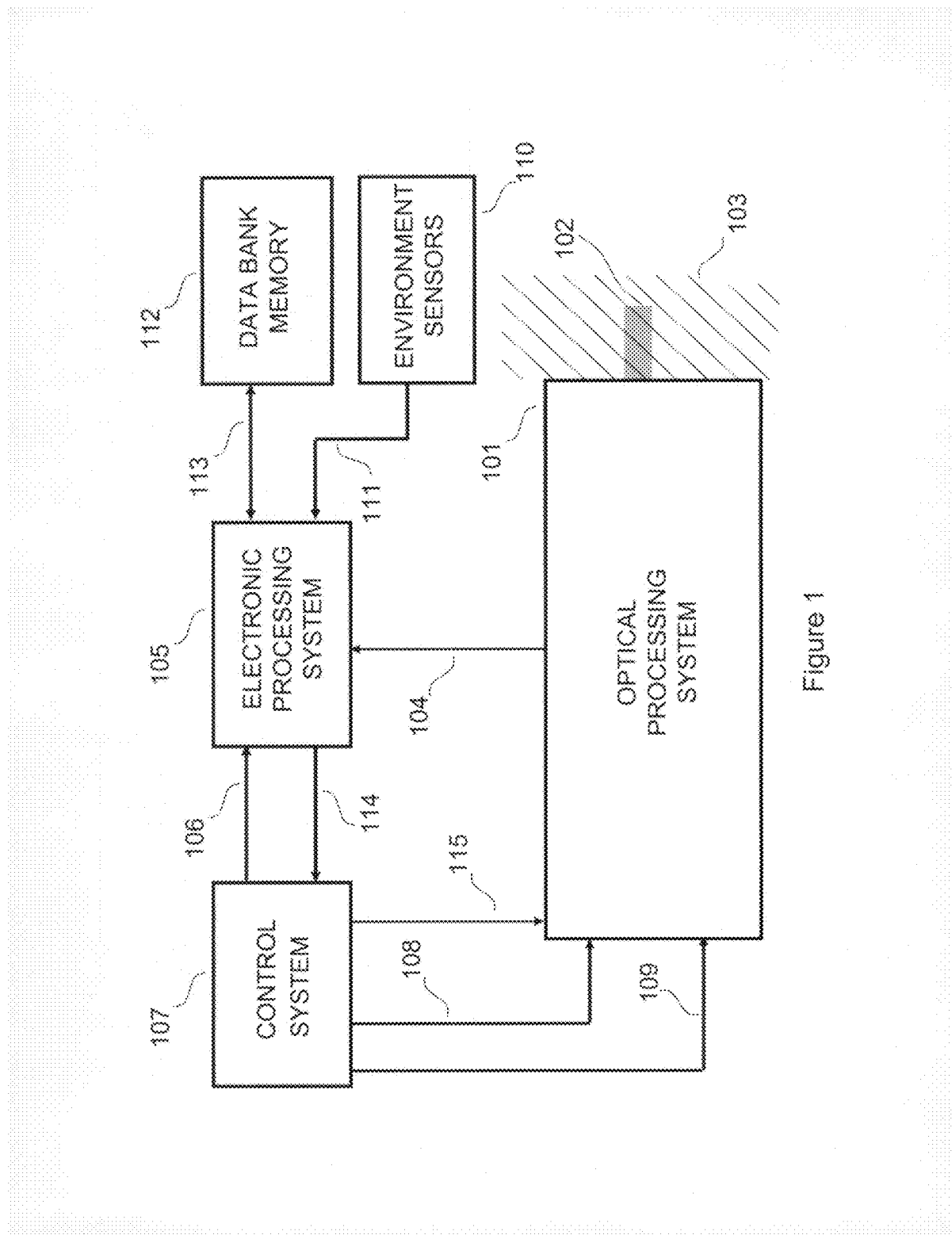
FIG. 1 is an illustration of the non-invasive analysis system according to the invention.

Optical coherence tomography is a non-invasive analysis technique typically based on splitting the output radiation of an optical source into probe radiation and reference radiation and of controlling aspects of either the optical source radiation or the reference radiation to accomplish a depth scan a target, such as tissue. In analysis applications, such as determining the concentration of glucose in tissue, typically multiple depth scans are averaged.

In the application of which this is a continuation-in-part, a non-invasive analysis system applies probe radiation to the target to be analyzed, re-combines the probe radiation with reference radiation interferometrically, to generate concurrent interferometric signals which are detected and correlated with previously stored electronic data to determine an attribute of the target.

Advantages of this approach include acquiring complete sets of interference signals concurrently, and correlating the interference signal data set with previously stored data sets, rather than assuming a simplified model of the target. Correlating data sets (or maps of data) with reference data sets (or fiducial maps of data) does not require making simplistic assumptions or using an approximate model.

Correlating data sets with reference fiducial maps of data does not assume a uniform distribution of scatterers, which allows more accurate representation of actual tissue. In general, correlating a data set with fiducial maps does not require an accurate understanding or description of the mechanism that causes the interference signals. Ideally, other factors that influence the interference signals can be compensated for by means of environment sensors and the attribute of the target that is to be determined has a dominant effect on the interference signals.

For purposes of this application "concurrently" includes simultaneously or at a high speed with respect to motion artifacts. Similarly concurrent signals includes simultaneous signals and also signals occurring at a high speed with respect to motion artifacts, thereby making such signals insensitive to motion artifacts. For purposes of this application an environment sensor is any sensor that measures a factor that also affects the interference signals.

Techniques for acquiring interference signals from multiple depths, either simultaneously or at high speed and therefore concurrently, are described in patent applications incorporated herein by reference. These techniques include, but are not limited to: simultaneously generating interference signals corresponding to different depths in a manner that different signals have different frequency content and therefore can be separated by electronic filtering; and high speed electronic scanning using two mode-locked lasers that are mode-locked frequency at different frequencies.

Sets of concurrent signals from various depths and from multiple spatially separated locations of the target can be acquired either by using broad area radiation to generate multiple beams of probe radiation or by sequentially translating a single narrow beam of probe radiation to the different spatially separated locations. In general such a beam or beams of probe radiation are referred to as probe radiation. The various depths from which signals are to be analyzed would be determined by characteristics of the source or reference radiation or by timing signals or by combinations thereof.

Ideally the various depths determined would accurately and repeatedly correspond to corresponding depths in the tissue being monitored. In practical use, the tissue may be distorted by, for example, the pressure of applying the monitor to skin. Such distortions can be compensated for by measuring the distorting influence. For example, including strain gauges to measure stresses and using these measurements to compensate for the distorting influences. Compensation can be achieved by adjusting the nominal depth to account for such distortions.

Also, ideally using fixed intensity probe radiation would accurately and repeatedly result in the same probe intensity at the various depths and spatial locations. In practical use, changes in skin surface, deviations from normal incidence of the probe radiation with respect to the skin surface and distorting influences, such as pressure, all contribute to modifying the actual probe intensity reaching different depths and spatial locations. These modifying influences can be compensated for by measuring the influences and compensating for them by adjusting the measured intensities of the various interference signals detected.

Techniques for achieving compensation are described in the application of which this is a continuation-in-part. In general these compensating techniques are herein referred to as normalizing the detected spatially separated interference signals. The resulting set of normalized signal intensities constitute a normalized interference signal map of the tissue.

In the application of which this is a continuation-in-part, such interference signal maps were then correlated with a data bank stored in memory. The data bank contains reference data sets or fiducial maps of the attribute of the target corresponding to different normalized interference signals at the various depths and spatial locations.

The accuracy of this approach is degraded by interfering effects, such as distortion, that are not completely compensated for and therefore have residual influence. In the present invention, rather than solely relying on measuring an interfering effect by means of an environment sensor, such as a pressure gauge, the sets of concurrently acquired data are effectively further processed prior to correlation.

This present approach enables residual interfering influences to be reduced or eliminated. Furthermore, the present invention enables compensation for some interfering effects without the necessity of using environment sensors to measure the interfering influence. The present approach also provides greater insensitivity to motion artifacts in the case of simultaneously acquired signals and reduces the magnitude with which scanning speeds need to be high with respect to motion artifacts.

A preferred embodiment of the non-invasive system associated with this invention is illustrated in and described with respect to FIG. 1. The following description relates to the application of the invention to glucose monitoring, however, the invention has a broad range of applications. In general the invention is a method, apparatus and system for determining an attribute of a target. In the glucose application the target is tissue and the attribute to be determined is the glucose level.

In the preferred embodiment, an optical processing system 101 generates probe radiation 102 and applies a portion of it to a target 103 which generates back-scattered radiation, which is interferometrically analyzed by the optical processing system and resultant interference signals are detected by an opto-electronic detector. The resultant electronic signals 104 are fed to an electronic processing system 105.

The electronic processing system 105 also receives timing signals 106 from a control system 107 which controls the optical source and any modulating or positioning elements in the optical processing system 101 by means of electronic control signals 108 and modulating signals 109. The electronic processing system 105 also receives data, by means of electronic environment sensor signals 111, from environmental sensors 110, which can include measuring, surface pressure, blood pressure and temperature.

The electronic processing system 105 also retrieves previously stored data from data bank memory 112, such as flash or disc memory, which contains correction data to compensate for varying sensor readings and also contains fiducial maps of glucose level data that correspond to various combinations of detected interference signals and sensor readings. The electronic processing system 105 communicates with the data bank memory 112 by means of an address/data bus 113 that is a conventional address/data bus or in the case of a remote data bank by, for example, wireless cellular phone technology, herein also referred to as an address/data bus.

According to the present invention, the electronic processing system 105 also processes the detected signals to determine an attribute of a target, which in the preferred embodiment is the concentration of glucose in tissue, by fitting multiple sets of concurrently acquired data to a profile template (or fiducial map) by techniques, including but not limited to, calculating a variance between the profile template and acquired data sets. For purposes of this invention, variance includes any measurement of the deviation of the acquired data sets from the profile template, including but not limited to: standard deviation; and sum of squares of distances.

Data sets that have a large variance (outlying data-sets) may be discarded and the profile template is refined to minimize the variance between at least some of the concurrently acquired data sets to generate a refined profile. The refined profile is correlated with data from a data bank stored in memory, and the resulting correlation data is processed and the output is communicated to devices, including but not limited to, a display device, a storage device, or a further processing device. In the preferred embodiment the correlation data is processed to determine the concentration of glucose in tissue (the attribute of the target). The resulting concentration value is displayed, stored or transmitted so as to, for example, assist a diabetic in controlling a glucose level.

Figure 2:
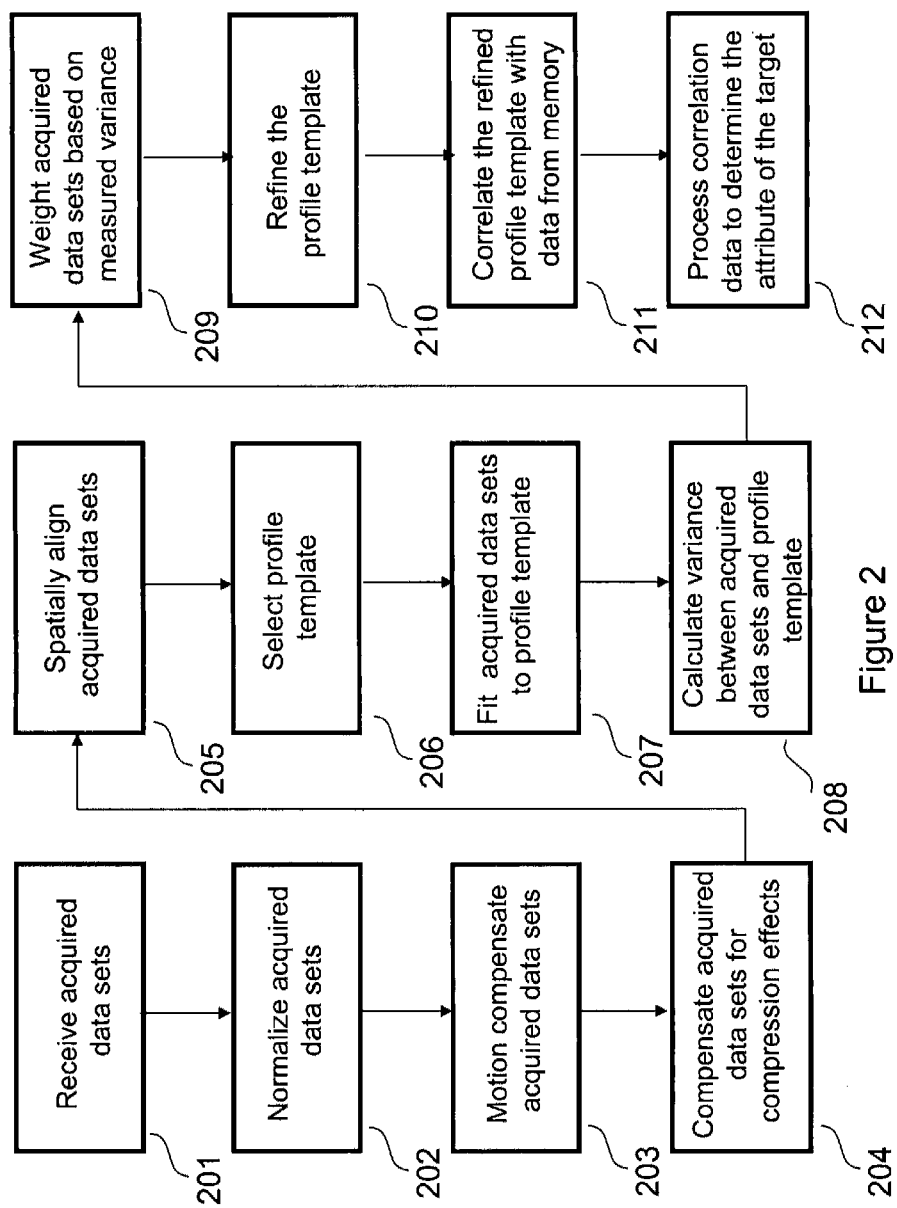
FIG. 2 is a flow chart illustration of the processing module of the non-invasive analysis system.

The processing in the preferred embodiment is illustrated in more detail and described with respect to FIG. 2. A profile template is selected which is an estimated representation of aspects of the target. The representation may be in one or more domains, including but not limited to, the time domain, the frequency domain and the spatial domain or may be in a combination of domains. Such profiles are further illustrated and described in FIG. 3.

Concurrently acquired data sets are received from the optical processing system. The data sets are normalized to compensate for known environment influences, such as temperature or intensity variations. The multiple concurrently acquired data sets acquired along substantially the same line or lines (substantially perpendicular to the target surface) into the target are spatially aligned to compensate for relative motion occurring between the target and the optical processing system.

This is accomplished by measuring such motion with conventional techniques (referred to environment sensors), or by analyzing aspects of successive depth scans. An astigmatic focusing element (or lens), such as used in the optical pick-up unit of DVD players could be used as a motion measuring environment sensor. A suitable depth scan (or acquired data set) aspect for such motion measurement is the interference signal from the front surface of the target. This aspect is further illustrated and described in FIG. 4.

In the preferred embodiment the optical processing system is loosely coupled to the front surface of the target, (the skin surface) and therefore does not cause any compression of the target (the tissue). In an alternative embodiment the optical processing system is coupled to the front surface of the target by means of an interface material with well-defined front and rear surfaces that can have index matching or optimizing properties and can be compressible.

In the case of a compressible interface material, the degree of compression can be measured by conventional means, such as strain gauges (referred to as environment sensors), or by analyzing the acquired data sets to determine the location of the front and rear surfaces of the interface material. The magnitude of compression measured in the interface material is used to compensate for compression in the target (tissue)

As illustrated in FIG. 2, the electronic processing system (105 of FIG. 1) performs the steps of: receiving acquired data sets 201 from the optical processing system; normalizing acquired data sets 202; motion compensating acquired data sets 203; optionally compression compensating acquired data sets 204; spatially aligning acquired data sets 205; selecting a profile template 206; fitting multiple sets of concurrently acquired data to the profile template 207; calculating a variance between profile template and acquired data sets 208; weighting acquired data sets based on the measured variance 209; refining the profile template 210 to minimize said variance between some of the acquired data sets to generate a refined profile correlating the refined profile 211 with data from a data bank stored in memory to generate correlation data; processing the correlation data 212 to determine the attribute of the target, which in the preferred embodiment is the concentration of glucose in tissue.

An example of a profile template which is an estimated representation of aspects of the back scattered profile of light by tissue (the target) is illustrated in FIG. 3A. This profile template corresponds to the target illustrated in FIG. 3B, where the probe radiation is applied to the target along the line 301 which is substantially normal (or perpendicular) to the surface of the target 302 (depicted as 103 in FIG. 1). Radiation scattered by the target back along the same line is detected and analyzed.

FIG. 3 illustrates the embodiment which includes the interface material, the location of the front surface is indicated by the dashed arrow 303, while the location of the rear surface is indicated by the dashed arrow 304. The profile template 305 is a representation in the spatial domain and the peaks indicated by the dashed arrows represent the front and rear surfaces of the interface material.

A concurrently acquired data set contains data corresponding to different regions of the profile template. For example, data acquired using the multiple reference scanning approach described in an application incorporated by reference could contain information corresponding to the regions indicated by the marks enclosed in the dashed oval 306.

For example, the mark 307 corresponds to the eighth reference signal and scans a region of the profile template indicated by the two solid arrows 308. Each of the marks enclosed in the dashed oval 306 can be regarded as a subset of the sets of concurrently acquired data and can be matched with their corresponding regions of the profile template to achieve spatial alignment.

Compression compensation can be achieved by processing the subset scans corresponding to the front and rear surfaces of the interface material (indicated by dashed arrows 303 and 304). Compensation can consist of modifying the spatial relationship between the higher order subset scans and the profile template.

Motion compensation is further described with respect to the depth scans illustrated in FIG. 4 where three successive depth subset scans of the surface of the target are shown. FIG. 4A shows a time domain scan of the target's front surface. In the case of a multiple reference analysis system (described in an application incorporated herein by reference), this scan (or subset scan) would correspond to the first reference signal in the case of a loosely coupled system and the second reference signal in the case where an interface material is included.

Such subset scans (or scans associated with a particular reference signal) can be readily separated from the detected interference signal by filtering in the analog electronic domain or digital signal processing (which can include filtering) in the digital domain.

The scan in FIG. 4A is well aligned with the target surface. FIG. 4B illustrates a similar scan where the scan and the front surface are misaligned by an amount indicated by the offset 401 (the distance between the maximum peaks in FIGS. 4A and 4B). FIG. 4C illustrates a similar scan where the scan and the front surface are misaligned by an additional amount indicated by the additional offset 402.

The magnitude of offsets, such as 401 and 402, provides a measurement of the location of the target's front surface, while the difference in the magnitude of successive offsets provides a measurement of the motion of the target. This measurement can include velocity and acceleration aspects. The resulting measurement of the motion of the target may be used to compensate for motion in acquired data sets.

The resulting measurement of the motion of the target may also be used as feedback to control the location of the optical processing system to minimize motion and optimize alignment. It can also be processed using predictive techniques to optimized motion compensation of the acquired data sets and feedback control of the location of the optical processing system.

Actual acquired signals contain noise and therefore do not necessarily exactly correspond to a profile template. Part of the selection process of a profile template can include calculating the variance (for example by performing a least square fit) between a profile template and acquired data sets. During this process, acquired data sets may be weighted on the basis of their variance from the profile template and those with a particularly large variance may be discarded.

The profile template with the best fit with the acquired data sets is selected and may be further processed by refining some of its characteristics to provide an even better fit with the acquired sets of data. The resulting refined profile is correlated with data from a data bank and the resulting correlation data is processed to determine an attribute of the target, such as the glucose concentration of tissue.

Profile templates may also be selected on the basis of registration marks on the target. Also sets of concurrently acquired data may be spatially aligned by using such registration marks. With this approach, effectively three dimensional profile templates may be used to more accurately correspond with the actual characteristics of a target. Such profile templates (or parameters of such profile templates) may be modified to track slowly changing aspects of the target.

Profile templates can be generated from a formula which may be a theoretical model of the target or of the system and target interaction or by processing multiple data sets to refine an initial estimated profile template. Over a period of time multiple profile templates may be generated corresponding to different environment sensor values and corresponding to multiple spatial relationships with registration marks.

The above description of the preferred embodiment illustrates a glucose level monitoring application of the invention, however, the invention has many potential applications, including but not limited to: imaging a target (in which case the image is the attribute of the target that is to be determined; bio-metric analysis; defect analysis of artifacts; authentication of documents, such as bank notes.

It is understood that the above description is intended to be illustrative and not restrictive. Many of the features have functional equivalents that are intended to be included in the invention as being taught. Many variations and combinations of the above embodiments are possible, for example, while the profile template described in the preferred embodiment is a spatial domain representation of the target, profile templates could include frequency domain and or time domain aspects in addition to or instead of spatial domain aspects.

The motion estimation illustrated in FIG. 4 involves measuring the distance between the maximum peaks in an interference signal. Other characteristics of the interference signal could be used to measure motion. For example, their rate of decay of the interference signal, or relative frequency content (exploiting Piezo speed decreasing towards scan extremities) could be used to measure motion.

Radiation could be generated by an array of optical sources, such as a VCSEL array (Vertical Cavity Surface Emitting Laser array), an edge emitting laser array, an SLD array or an LED array rather than a single optical source. Such arrays could be collimated by an array of micro-lens, which could be spatially matched with a multi-segment detector. An advantage of using such arrays is that there is reduced sensitivity to cross-talk between adjacent optical signals because they are incoherent with respect to each other. The first and second mode-locked lasers could be mode-locked laser diodes or mode-locked micro-lasers.

Acquiring concurrent data sets from the target can be accomplished in many ways, including but not limited to: using a broadband source and the multiple reference (or multiple zone) techniques described in the applications incorporated by reference; using a broadband source and conventional electromechanical or acousto-optic scanning techniques; by using a laser source that can be tuned at high speed over a broad wavelength range; using a pair of mode locked lasers with slightly different mode-locked frequencies.

The invention is applicable to various forms of optical coherence tomography, including but not limited to, conventional time domain scanning OCT; multiple reference based systems; Fourier OCT using either a wavelength swept source or spectral OCT using a diffraction grating to separate wavelengths. The embodiments described use optical radiation, however the invention is not restricted to optical radiation. The invention could use other forms of radiation, including but not limited to, acoustic radiation such as ultra-sound, and other forms of electromagnetic radiation such as micro-wave or x-ray radiation.

The scope of this invention should therefore not be determined with reference to the above description, but instead should be determined with reference to the appended claims and drawings, along with the full scope of equivalents to which such claims and drawings are entitled.

What is claimed is:

1. A method of determining an attribute of a target, comprising:
    fitting multiple sets of concurrently acquired data to a profile template, where said multiple data sets were acquired using interference signals;
    calculating a variance between said profile template and said data sets;
    refining said profile template to minimize said variance between at least some of said concurrently acquired data sets to generate a refined profile;
    correlating said refined profile with data from a data bank stored in memory to generate correlation data; and
    processing said correlation data to determine said attribute of said target.

2. The method of claim 1, further including the step of normalizing the sets of concurrently acquired data.

3. The method of claim 1, further including the step of spatially aligning the sets of concurrently acquired data.

4. The method of claim 3, further including the step of spatially aligning the sets of concurrently acquired data by matching subsets of the sets of concurrently acquired data with a profile.

5. The method of claim 3, further including the step of spatially aligning the sets of concurrently acquired data by compensating for motion effects.

6. The method of claim 3, further including the step of spatially aligning the sets of concurrently acquired data by compensating for compression effects.

7. The method of claim 3, further including the step of spatially aligning the sets of concurrently acquired data by using registration marks.

8. The method of claim 1, further including the step of weighting the sets of concurrently acquired data sets on the basis of their variance from a profile.

9. The method of claim 1, further including the step of generating the profile template from a formula.

10. The method of claim 1, further including the step of generating the profile template by processing data sets.

11. The method of claim 1, further including the step of modifying the sets of concurrently acquired data using data related to an environment sensor signal.

12. The method of claim 1, wherein the step of processing said correlation data to determine said attribute of said target further includes processing the target of tissue.

13. The method of claim 1, wherein the step of processing said correlation data to determine said attribute of said target further includes processing to determine a glucose concentration level.

14. The method of claim 1, wherein the step of processing said correlation data to determine said attribute of said target further includes processing to determine a bio-metric characteristic.

15. The method of claim 1, wherein the step of processing said correlation data to determine said attribute of said target further includes processing to determine an image of the target.

16. An improved system for determining an attribute of a target, said system comprising an optical system adapted to generate probe radiation and reference radiation, said optical system configured to apply at least a portion of said probe radiation to said target to generate back-scattered radiation and configured to combine said back-scattered radiation with said reference radiation to produce an interference signal; a detector adapted to detect said interference signal; a control system configured to control said optical system and an electronic processing system; a memory storing data in a data bank; an electronic processing system extracting concurrent information from detected interference signal, and correlating said extracted concurrent information with said data to generate correlation data, said improvement comprising:
    a processing system adapted to fit multiple sets of concurrently acquired data to a profile template, to calculate a variance between said profile template and said data sets, to refine said profile template to minimize said variance between at least some of said concurrently acquired data sets to generate a refined profile, to correlate said refined profile with data from a data bank stored in memory to generate correlation data, and to process said correlation data to determine said attribute of said target.

17. A non-transitory computer readable medium containing an executable program for generating and communicating some determination concerning a target whose attributes are under test, where the program performs the steps of:
    fitting multiple sets of concurrently acquired data to a profile template;
    calculating a variance between said profile template and said data sets;
    refining said profile template to minimize said variance between at least some of said concurrently acquired data sets to generate a refined profile;
    correlating said refined profile with data from a data bank stored in memory to generate correlation data; and
    processing said correlation data to determine said attribute of said target.

* * * * *